United States Patent
Bratslavsky et al.

(10) Patent No.: US 9,810,694 B2
(45) Date of Patent: Nov. 7, 2017

(54) IDENTIFICATION OF FULLY HUMAN ANTIBODIES FOR USE IN THERAPY AND DIAGNOSIS OF HUMAN DISEASES

(71) Applicants: Gennady Bratslavsky, Fayetteville, NY (US); Ilya Tsimafeyeu, Mogilev (BY)

(72) Inventors: Gennady Bratslavsky, Fayetteville, NY (US); Ilya Tsimafeyeu, Mogilev (BY)

( * ) Notice: Subject to any disclaimer, the term of this patent is extended or adjusted under 35 U.S.C. 154(b) by 0 days.

(21) Appl. No.: 14/819,500

(22) Filed: Aug. 6, 2015

(65) Prior Publication Data

US 2017/0038392 A1  Feb. 9, 2017

(51) Int. Cl.
*G01N 33/68* (2006.01)
*G01N 33/574* (2006.01)

(52) U.S. Cl.
CPC ... *G01N 33/6854* (2013.01); *G01N 33/57434* (2013.01); *G01N 2500/10* (2013.01)

(58) Field of Classification Search
None
See application file for complete search history.

(56) References Cited

U.S. PATENT DOCUMENTS 4,868,107 A * 9/1989 Roy, III ............. G01N 33/5308 435/7.95
8,343,761 B2  1/2013 Tsuchiya et al.

OTHER PUBLICATIONS

Palmeira et al. (Clinical and Developmental Immunology 2012, ).*
Yang et al. (Critical Reviews in Oncology/Hematology 2001, vol. 38, p. 17-23).*
Heo et al. (BMB Reports p. 677-685, year 2012).*
Roger R. Beerli et al. Isolation of human monoclonal antibodies by mammalian cell display Proc Natl Acad Sci USA. Sep. 23, 2008; 105(38): 14336-14341.
Scheeren FA et al. Antigen-specific monoclonal antibodies isolated from B cells expressing constitutively active STAT5. PLoS One. Apr. 15, 2011;6(4):e17189.
Reddy ST et al. Monoclonal antibodies isolated without screening by analyzing the variable-gene repertoire of plasma cells. Nat Biotechnol. Sep. 2010;28(9):965-9.
Huang J, et al. Broad and potent neutralization of HIV-1 by a gp41-specific human antibody. Nature. Nov. 15, 2012;491(7424):406-12.
Duvall MR et al. Different approaches for obtaining antibodies from human B cells. Curr Drug Discov Technol. Mar. 2014;11(1):41-7.

* cited by examiner

*Primary Examiner* — Jacob Cheu
(74) *Attorney, Agent, or Firm* — Aleksandr Smushkovich

(57) ABSTRACT

The present invention is drawn to methods for detection of the fully human antibodies infiltrated into a solid tissue, and to optimize methods for generating, selecting, and expanding monoclonal antibodies to large numbers for antibody-based therapy and diagnosis. The invention is exemplified in a number of implementations and applications, some of which are summarized below and throughout the specification.

In one aspect, the invention is directed to methods for identifying potentially therapeutic fully human antibodies that have infiltrated a solid tissue comprising the following steps: (a) detecting and sorting into one or more subsets a sample of antibodies from an accessible tissue of an individual; (b) characterization of the fully human antibodies; (c) production and purification of the fully human antibody; (d) assessment of the therapeutic and diagnostic activity of fully human antibody.

In another aspect, the invention is directed to methods of use of fully human antibodies identified from tissue for diagnosis and treatment of human diseases, wherein such method comprises the steps of: (a) small or large scale production and purification of the fully human antibody; (b) administration of the pharmaceutically acceptable fully human antibody in humans for diagnosis and treatment of diseases.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

8 Claims, 4 Drawing Sheets

Anti-VEGF fully human antibody of the present invention inhibited proliferation of endothelial cells in vitro.

Inhibitory effects of anti-VEGF fully human antibody of the present invention on cancer cells proliferation *in vitro*

Anti-VEGF fully human antibody of the present invention inhibited tumor growth compared with anti-VEGF humanized antibody and vehicle *in vivo*.

Anti-EGFR fully human antibody of the present invention inhibits MDA-MB-468 breast cancer cells proliferation.

Anti-EGFR fully human antibody of the present invention significantly inhibits growth of colon cancer xenograft.

Anti-FGFR1 fully human antibody of the present invention dose dependently inhibited proliferation of lung cancer cells.

Anti-FGFR1 fully human antibody of the present invention significantly inhibits growth of lung cancer xenograft.

Anti-EGFR fully human antibody of the present invention is more effective than other fully human antibody (panitumumab) in vivo.

SEQUENCE LISTING

```
<160> NUMBER OF SEQ ID NOS: 2

<210> SEQ ID NO 1
<211> LENGTH: 107
<212> TYPE: PRT
<213> ORGANISM: Homo sapiens

<400> SEQUENCE: 1

Ala Arg Ala Pro Ser Ile Val Thr Thr Leu Ser Lys Val Phe Pro Pro
1               5                   10                  15

Glu Gln Leu Leu Lys Ser Gly Ala Thr Ser Asp Ser Val Cys Val Asn
            20                  25                  30

Phe Pro Tyr Arg Thr His Gln Glu Ala Lys Val Gln Trp Lys Val Ala
        35                  40                  45

Gly Gln Asn Ser Glu Thr Glu Ser Val Gln Ser Asp Lys Asp Ser Thr
    50                  55                  60

Phe Thr Leu Tyr Ser Val Tyr Ser Lys Ser Ala Asp Asn Asp Tyr Glu
65                  70                  75                  80

Lys His Ala Cys Glu Leu Leu Asn Val Gly Leu Ser Ser Pro Val Gly
                85                  90                  95

Glu Thr Phe Lys Ser Asn Arg Leu Gln Ser Cys
            100                 105

<210> SEQ ID NO 2
<211> LENGTH: 320
<212> TYPE: PRT
<213> ORGANISM: Homo sapiens

<400> SEQUENCE: 2

Pro Gly Lys Ser Lys Ser Tyr Phe Thr Pro Ser Val Tyr Pro Leu Ile
1               5                   10                  15

Gly Ser Ala Leu Asn Gly Ala Gln Thr Asn Ser Cys Arg Val Asn Ser
            20                  25                  30

Ala Thr Phe Pro Glu Ser Lys Leu Asn Val Pro Val Thr Val Thr Trp
        35                  40                  45

Asn Ser Gly Val His Thr Phe Pro Ala Val Leu Glu Ser Asp Leu Tyr
    50                  55                  60

Thr Leu Ser Ser Ser Val Pro Thr Glu Ser Ser Pro Arg Pro Ser Glu
65                  70                  75                  80

Thr Val Thr Val Val Asp Cys Asn Ser Thr Lys Val Asp Lys Asp Asp
                85                  90                  95

Val Glu Val His Thr Ala Lys Ile Pro Arg Gln Pro Asp Cys Gly Cys
            100                 105                 110
```

```
              -continued

Lys Pro Cys Ile Cys Thr Pro Glu Ile Phe Pro Ala Lys Pro Lys Asp
        115             120             125

Val Leu Thr Thr Ile Thr Leu Thr Pro Lys Cys Val Ile Ser Lys Asp
130         135             140

Asp Gly Tyr Pro Glu Val Gln Phe Ser Val Ala His Pro Ala Ser Trp
145             150             155             160

Phe Val Gln Thr Arg Glu Glu Gln Phe Asn Ser Val Ser Ser Val Phe
                165             170             175

Thr Phe Arg Ser Val Ser Glu Thr Asn Leu Pro Ile Met His Gln Asp
            180             185             190

Trp Lys Glu Phe Lys Phe Pro Ala Pro Ile Glu Lys Thr Ile Thr Ala
        195             200             205

Lys Lys Arg Pro Lys Ala Pro Gln Val Tyr Thr Ile Pro Leu Gly Cys
        210             215             220

Leu Val Lys Pro Pro Lys Glu Gln Met Ala Lys Asp Lys Val Ser Leu
225             230             235             240

Thr Tyr Gln Lys Cys Met Pro Ile Thr Asp Phe Phe Pro Glu Asp Ala
            245             250             255

Pro Thr Val Glu Trp Gln Trp Asn Gly Met Val Gln Pro Ala Glu Asn
            260             265             270

Tyr Lys Asn Thr Gln Pro Ile Met Asn Gly Val Ser Asn Trp Glu Gly
        275             280             285

Ser Leu Ser Ser Ala Gly Asn Thr Phe Thr Cys Ser Val Thr Val Leu
        290             295             300

His Glu Gly Leu His Asn Pro His His Lys Ser Leu Ser His Ser Thr
305             310             315             320
```

IDENTIFICATION OF FULLY HUMAN ANTIBODIES FOR USE IN THERAPY AND DIAGNOSIS OF HUMAN DISEASES

BACKGROUND OF THE INVENTION

Antibody-based therapy is now one of the most successful and important strategies for treating patients with haematological malignancies, solid tumors, infections, rheumatic and vascular diseases. Evidence from clinical trials of antibodies in patients has revealed the importance of iterative approaches for the selection of antigen targets and optimal antibodies, including the affinity and avidity of antibodies, the choice of antibody construct, the therapeutic approach (such as signalling abrogation or immune effector function) and the need to critically examine the pharmacokinetic and pharmacodynamic properties of antibodies in early clinical trials.

Based on technologies of monoclonal antibodies generation, there are several types of therapeutic antibodies including polyclonal and monoclonal antibodies, murine, chimeric, humanized and fully human antibodies.

Monoclonal antibodies are monospecific antibodies that are made by identical immune cells that are all clones of a unique parent cell, in contrast to polyclonal antibodies which are made from several different immune cells. Monoclonal antibodies have monovalent affinity, in that they bind to the same epitope. Although serum polyclonal antibody preparations have been clinically effective in many cases, problems related to toxicity including a risk for allergic reactions, lot-to-lot variation, and uncertain dosing have limited their use. In addition, the active antigen-specific antibodies in a polyclonal preparation typically represent a relatively small portion of the total antibodies (1%); the rest of the antibodies are not only ineffective but could be even toxic or immunogenic.

The beginning of the paradigm change for antibodies began with the publication of the seminal article (Kohler G, Milstein C. Continuous cultures of fused cells secreting antibody of predefined specificity. Nature. 1975; 256:495-497) describing hybridoma technology which can provide unlimited quantities of monoclonal antibodies with predefined specificity. In addition, this technology was not patented and could be used freely. A major limitation of the hybridoma technology has been the inability to produce human monoclonal antibodies. Administration of murine monoclonal antibodies in humans resulted in immune responses against the foreign proteins with the generation of human anti-mouse antibodies (HAMAs). However, the advent of a number of molecular biology techniques, mostly recombinant DNA technology, and the increased understanding of the antibody structure and function led to the development of chimeric and humanized monoclonal antibodies. Finally, phage-display techniques and other techniques based on the progress of molecular biology, including the generation of transgenic animals, allowed the development of fully human antibodies; these methodologies have been extensively reviewed. Fully human monoclonal antibodies are highly desirable as therapeutics, for in addition to the advantages of being very specific for and tightly binding to their therapeutic targets, fully human antibodies avoid potential immune responses that may occur in patients receiving antibodies that contain nonhuman (typically mouse) components. However, during the last decade the basic concepts and methodologies for fully human antibody generation have not changed significantly but have been applied to numerous new targets.

It would be highly useful to the medical and scientific fields to investigate alternate strategies for generating of fully human antibodies to improve efficacy of therapy and to produce conceptually new antibodies for treatment of different diseases.

SUMMARY OF THE INVENTION

The present invention is drawn to methods for detection of the fully human antibodies infiltrated into a solid tissue, and to optimize methods for generating, selecting, and expanding monoclonal antibodies to large numbers for antibody-based therapy and diagnosis. The invention is exemplified in a number of implementations and applications, some of which are summarized below and throughout the specification.

In one aspect, the invention is directed to methods for identifying potentially therapeutic fully human antibodies that have infiltrated a solid tissue comprising the following steps: (a) detecting and sorting into one or more subsets a sample of antibodies from an accessible tissue of an individual; (b) characterization of the fully human antibodies; (c) production and purification of the fully human antibody; (d) assessment of the therapeutic and diagnostic activity of fully human antibody.

In another aspect, the invention is directed to methods of use of fully human antibodies identified from tissue for diagnosis and treatment of human diseases, wherein such method comprises the steps of: (a) small or large scale production and purification of the fully human antibody; (b) administration of the pharmaceutically acceptable fully human antibody in humans for diagnosis and treatment of diseases.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

DETAILED DESCRIPTION OF THE INVENTION

Figure 1:
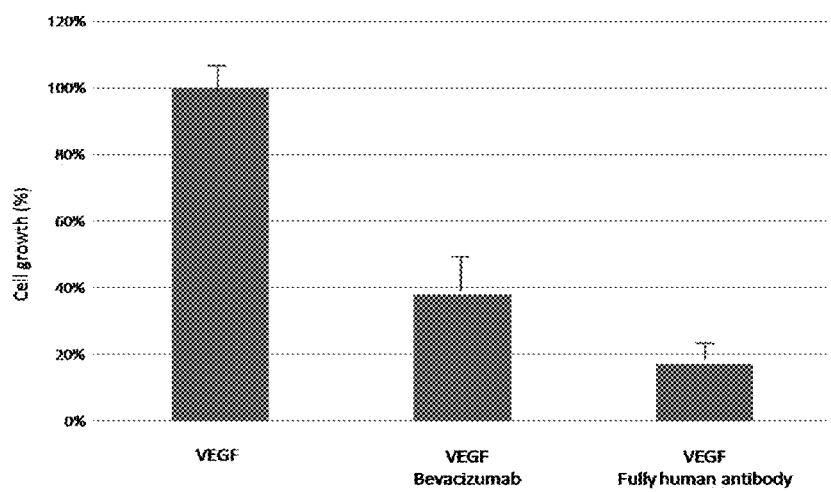
FIG. 1. Anti-VEGF fully human antibody of the present invention inhibited proliferation of endothelial cells in vitro.

The potentially therapeutic or diagnostic fully human antibodies of the present invention are those derived from human tissues with further possibility to be purified, scale-up produced appropriate quantities and used in treatment or diagnosis of human diseases as pharmaceutical agents.

The invention is directed to methods of determining the types and numbers of potentially therapeutic or diagnostic fully human antibodies infiltrated into a solid tissue (biologic materials), such as a tumor, tissue affected by an autoimmune disease, a tissue affected by graft versus host disease (GVHD), a normal tissue, blood plasma, placenta, or the like. Although solid tissues of interest are usually disease-affected solid tissue, in some embodiments, the levels and/or numbers and/or ratios of different subsets of antibodies in normal tissues may also be used to determine potentially therapeutic or diagnostic fully human antibodies.

Previously some authors have described methods of isolating antibodies from tissues for therapy or diagnosis [Masayuki Tsuchiya, et al. US20060235207, U.S. Pat. No. 8,343,761; Sahin Ugur, et al. WO2000020460; Gingeras, Thomas, et al. WO1994011507; Natalie Sutkowski, et al. U.S. Pat. No. 8,715,743; Christoph Esslinger, et al. U.S. Pat. No. 8,519,106; Sai Reddy, et al. US20110312505]. These methods relates to isolation of antibodies from derived B cells or plasma cells infiltrating human tissues. The main difference of present invention is that proposed method includes isolation of potentially therapeutic or diagnostic fully human antibodies from non-lymphoid tissues directly and further scale-up production of isolated antibodies for treatment and diagnosis of human diseases.

The practice of the present invention may employ, unless otherwise indicated, conventional techniques and descriptions of molecular biology (including recombinant techniques), cell biology, biochemistry, bioinformatics, immunologic techniques, and analytical chemistry techniques, such as mass-spectrometry, which are within the skill of the art. Such conventional techniques include, but are not limited to, sampling and analysis of human tissues, blood cells, polypeptides, peptides, proteins, including antibodies, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals. The preparation of the fully human antibodies from the tissues containing these antibodies and preparation therapeutically and diagnostic useful fully human antibodies can be carried out by any of the culture, recombinant and purification methods known in the art. Standard techniques may be used for syntheses, analyses, pharmaceutical preparation, formulation, and delivery, and treatment of patients.

Methods of identification of potentially therapeutic or diagnostic fully human antibodies that have infiltrated a solid tissue comprising the following steps: 1) to receive biologic materials from patient and normal donors; 2) to prepare biologic materials for detecting; 3) to identify one or multiple potentially therapeutic or diagnostic fully human antibodies in biologic materials using techniques described above; 4) to select one or multiple fully human antibodies for further investigation; 5) to characterize of selected fully human antibodies; 6) to evaluate potent therapeutic activity of the fully human antibodies and to determine possibility of use of fully human antibodies in diagnosis. Moreover, methods of detection includes production and purification of the selected fully human antibodies for investigation, but are not limited thereto.

In another aspect, the invention is directed to methods of use of selected fully human antibodies identified from tissue for diagnosis and treatment of human diseases, wherein such method comprises the steps of: 1) scale production and purification of the fully human antibody; 2) administration of the pharmaceutically acceptable fully human antibody in humans for diagnosis and treatment of diseases and pathological conditions. As used herein, the terms "illness", "disease", "medical condition", "pathological conditions", or "abnormal condition", are used interchangeably with the term "medical disorder".

The potentially therapeutic or diagnostic fully human antibodies of the present invention could be fully human monoclonal antibodies.

The globulin type of the fully human antibodies of the present invention is not particularly limited insofar as they have the ability to bind to specific antigen, and examples are IgG, IgM, IgA, IgE, IgD etc. The fully human antibodies of the present invention are not limited insofar as they possess the ability to bind to specific antigen, and they include not only those obtained directly from a human tissues such full-size and full-length human antibodies, but also fragments thereof prepared by enzymatic digestion, gene recombination, etc., and fusion proteins thereof with another protein or factor, etc. Such antibodies may be modified by gene recombination insofar as their ability to bind to specific antigen is not deteriorated.

In particular, the antiangiogenic fully human antibodies of the present invention neutralize the vascularization activity of different human growth factors and their receptors. This vascularization is a phenomenon consisting of the steps (1) destruction and degradation of basement membrane by proteases (i.e. decomposition of intercellular matrix protein), (2) migration of endothelial cells, (3) proliferation of endothelial cells, and (4) differentiation of endothelial cells and formation of tubes and cavities. Hence, it is considered that the vascularization can be inhibited by inhibiting at least one of these steps. The inhibition of vascularization by antibody can be checked by examination of the effect of the antibody on the reaction in each step. The fully human antibodies against angiogenic growth factors and their receptors of the present invention can inhibit the vascularization by inhibiting the proliferation, migration of vascular endothelial cells, or the blood vessels formation, as vascularization activities induced by human growth factors and/or their receptors.

For another example, anti-cancer fully human antibodies of the present invention inhibit cancer growth by one or more ways. In particular, antibodies can bind to the important antigen (target) on cancer cells, tumor stroma, circulating tumor cells, and other components of cancer pathogenesis. Moreover, antibodies can impact on different steps of immune response against cancer. For example, antibodies can block suppressive function of immune system or/and restore or enhance the immune system's ability to fight cancer.

In case of treatment of infections, anti-infective fully human antibodies of the present invention could neutralize one or more types of antigens depending on type of infection as well as type of antibody. Anti-inflammatory fully human antibodies of the present invention can block a number of cytokine- and chemokine-dependent cellular functions including neutrophil activation, up-regulation of the cell adhesion receptors, neutrophil chemotaxis and other steps of inflammation.

Antibodies of the invention that specifically bind to antigen may be useful in treatment of antigen-mediated diseases, as discussed below. Said antibodies can be used in binding assays to detect antigen binding and their capacity to inhibit antigen from forming any complex with antigen.

Conditions effectively treated by an antibody or pharmaceutical composition described herein include pulmonary diseases such as asthma, chronic obstructive pulmonary disease, pulmonary alveolar proteinosis, bleomycin-induced pneumopathy and fibrosis, radiation-induced pulmonary fibrosis, cystic fibrosis, collagen accumulation in the lungs, and ARDS. The disclosed antibodies and pharmaceutical compositions of the invention also are useful for treating broncho-pulmonary dysplasia (BPD); chronic obstructive pulmonary diseases (e.g. emphysema and chronic bronchitis), and chronic fibrotic lung disease of preterm infants. In addition, the compounds, compositions and combination therapies of the invention are used to treat occupational lung diseases, including asbestosis, coal worker's pneumoconiosis, silicosis or similar conditions associated with long-term exposure to fine particles. In other aspects of the invention, the disclosed compounds, compositions and combination therapies are used to treat bronchioliterans organizing pneumonia, pulmonary fibrosis, including idiopathic pulmonary fibrosis and radiation-induced pulmonary fibrosis; pulmonary sarcoidosis; and allergies, including allergic rhinitis, contact dermatitis, atopic dermatitis and asthma.

Such antibodies or pharmaceutical compositions are useful also for treating patients suffering from various skin disorders, including but not limited to dermatitis herpetiformis (Duhring's disease), atopic dermatitis, contact dermatitis, urticaria (including chronic idiopathic urticaria), and autoimmune blistering diseases, including pemphigus vulgaris and bullous pemphigoid. Other diseases treatable with antibodies include myasthenia gravis, sarcoidosis, including pulmonary sarcoidosis, scleroderma, reactive arthritis, hyper IgE syndrome, multiple sclerosis and idiopathic hypereosinophil syndrome. The combination is used also for treating allergic reactions to medication and as an adjuvant to allergy immunotherapy.

The antibodies and pharmaceutical compositions described herein are useful for treating of infectious diseases are caused by pathogenic microorganisms such as bacteria, viruses, fungi or protozoa. Cardiovascular disorders and injuries are treatable and/or preventable with disclosed either pharmaceutical compositions or antibodies alone or in combination with other compounds and methods. Cardiovascular disorders treatable include aortic aneurysms; including abdominal aortic aneurysms, acute coronary syndrome, arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure, congestive heart failure, cachexia of heart failure; myocardial infarction; restenosis and/or atherosclerosis after heart surgery or after carotid artery balloon angioplastic procedures; silent myocardial ischemia; left ventricular pump dysfunction, post implantation complications of left ventricular assist devices; Raynaud's phenomena; thrombophlebitis; vasculitis, including Kawasaki's vasculitis; veno-occlusive disease, giant cell arteritis, Wegener's granulomatosis; mental confusion following cardio pulmonary bypass surgery, and Schoenlein-Henoch purpura.

In certain embodiments, antibodies and pharmaceutical compositions of the invention can also be used to treat chronic pain conditions, such as chronic pelvic pain, including chronic prostatitis/pelvic pain syndrome, and post-herpetic pain.

Disorders of the endocrine system including juvenile onset diabetes (includes autoimmune diabetes mellitus and insulin-dependent types of diabetes) and maturity onset diabetes (includes non-insulin dependent and obesity-mediated diabetes) can also be treated with antibodies or pharmaceutical compositions of the invention. Such treatment includes secondary conditions associated with diabetes, such as diabetic retinopathy, kidney transplant rejection in diabetic patients, obesity-mediated insulin resistance, and renal failure, which itself may be associated with proteinurea and hypertension. Other endocrine disorders also are treatable with these compounds and include polycystic ovarian disease, X-linked adrenoleukodystrophy, hypothyroidism and thyroiditis, including Hashimoto's thyroiditis (i.e., autoimmune thyroiditis), thyroid cell dysfunction, including euthyroid sick syndrome.

Conditions of the gastrointestinal system are treatable or preventable with antibodies or pharmaceutical compositions of the invention, alone or in combination with other therapeutics. These conditions include coeliac disease, Crohn's disease; ulcerative colitis; idiopathic gastroparesis; pancreatitis, including chronic pancreatitis; acute pancreatitis, inflammatory bowel disease and ulcers, including gastric and duodenal ulcers.

Disorders of the genitourinary system are also treatable or preventable with antibodies or pharmaceutical compositions described herein. Such disorders include glomerulonephritis, including autoimmune glomerulonephritis, glomerulonephritis due to exposure to toxins or glomerulonephritis secondary to infections with haemolytic streptococci or other infectious agents. Also treatable with the compounds, compositions and combination therapies of the invention are uremic syndrome and its clinical complications (for example, renal failure, anemia, and hypertrophic cardiomyopathy), including uremic syndrome associated with exposure to environmental toxins, drugs or other causes. Complications that arise from inflammation of the gallbladder wall that leads to alteration in absorptive function are treatable or preventable with the antibodies of this invention. Included in such complications are cholelithiasis (gallstones) and choliedocholithiasis (bile duct stones) and the recurrence of cholelithiasis and choliedocholithiasis. Further conditions treatable with the compounds, compositions and combination therapies of the invention are complications of hemodialysis; prostate conditions, including benign prostatic hypertrophy, nonbacterial prostatitis and chronic prostatitis; and complications of hemodialysis.

Also provided herein are methods for using antibodies of the invention, compositions, and combination therapies to treat various hematologic and oncologic disorders. For example, antibodies, alone or in combination with other anticancer drugs or anticancer treatment, can be used to treat various forms of cancer, including solid tumors such as carcinomas and sarcomas, and hematological malignancies. For example, treatable cancers include lung cancer (non-small cell and small cell), mesothelioma, head and neck cancers, melanoma and skin cancers, osteosarcomas, soft tissue sarcomas and bone tumors, breast cancer, gastrointestinal cancers, genitourinary cancers, adrenal tumors, gastrointestinal stromal tumors, neuroendocrine tumors, germ cell tumors, tumors of central nervous system, hereditary cancer syndromes. Additional treatable cancers and conditions include leukemia, including acute myelogenous leukemia, chronic myelogenous leukemia, myeloid leukemia, chronic or acute lymphoblastic leukemia and hairy cell leukemia, multiple myeloma, Epstein-Barr virus-positive tumors, cancer-associated cachexia, fatigue, asthenia, paraneoplastic syndrome of cachexia and hypercalcemia. Other malignancies with invasive metastatic potential can be treated with the subject compounds, compositions and combination therapies.

In addition, the disclosed antibodies can be used to treat anemias and hematologic disorders, including chronic idiopathic neutropenia, anemia of chronic disease, aplastic anemia, including Fanconi's aplastic anemia; idiopathic thrombocytopenic purpura (ITP); thrombotic thrombocytopenic purpura, myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vaso-occlusive crisis.

Various lymphoproliferative disorders also are treatable with antibodies of the invention, including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma. Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sézary syndrome.

Hereditary conditions such as Gaucher's disease, Huntington's disease, linear IgA disease, and muscular dystrophy are treatable with the antibodies of this invention.

Other conditions treatable or preventable by the disclosed antibodies or pharmaceutical compositions include those resulting from injuries to the head or spinal cord including subdural hematoma due to trauma to the head. In connection with this therapy, the compositions and combinations described are suitable for preventing cranial neurologic damage and preventing and treating cervicogenic headache. The compositions and combinations described are further suitable for treating neurological side effects associated with brain irradiation.

Antibodies and pharmaceutical composition of the invention are also useful for treating conditions of the liver such as hepatitis, including acute alcoholic hepatitis, acute drug-induced or viral hepatitis, hepatitis A, B and C, sclerosing cholangitis, hepatic sinusoid epithelium, and inflammation of the liver due to unknown causes.

Non-arthritic disorders of the bones and joints and also treatable with the antibodies described herein. This encompasses osteoclast disorders that lead to bone loss, such as but not limited to osteoporosis, including post-menopausal osteoporosis, osteoarthritis, periodontitis resulting in tooth loosening or loss, and prosthesis loosening after joint replacement (generally associated with an inflammatory response to wear debris). This latter condition also is called "orthopedic implant osteolysis." Another condition treatable with the compounds, compositions and combination therapies of the invention is temporal mandibular joint dysfunction (TMJ).

Antibodies or pharmaceutical compositions of the invention can also be used to treat rheumatic disorders including adult and juvenile rheumatoid arthritis; scleroderma; systemic lupus erythematosus; gout; osteoarthritis; polymyalgia rheumatica; scronegative spondylarthropathies, including ankylosing spondylitis, and Reiter's disease, psoriatic arthritis and chronic Lyme arthritis. The antibodies of this invention are also useful for treating inflammation of the voluntary muscle and other muscles, including dermatomyositis, inclusion body myositis, polymyositis, and lymphangioleimyomatosis.

Another use for the antibodies and pharmaceutical compositions of the invention is the treatment and/or prevention of primary amyloidosis and the secondary amyloidosis that is characteristic of various condition including Alzheimer's disease, secondary reactive amyloidosis; Down's syndrome; and dialysis-associated amyloidosis. Also treatable with the antibodies or pharmaceutical compositions of the invention are inherited periodic fever syndromes, including familial Mediterranean fever, hyperimmunoglobulin D and periodic fever syndrome and TNF-receptor associated periodic syndromes (TRAPS).

In other embodiments, the antibodies or pharmaceutical compositions of the invention can be used to treat disorders involving the skin or mucous membranes. Such disorders include acantholytic diseases, including Darier's disease, keratosis follicularis and pemphigus vulgaris. Additional skin disorders that can be treated using antibodies of the invention include acne, acne rosacea, alopecia greata, aphthous stomatitis, bullous pemphigoid, burns, eczema, erythema, including erythema multiforme and erythema multiforme bullosum (Stevens-Johnson syndrome), inflammatory skin disease, lichen planus, linear IgA bullous disease (chronic bullous dermatosis of childhood), loss of skin elasticity, mucosal surface ulcers, including gastric ulcers, neutrophilic dermatitis (Sweet's syndrome), dermatomyositis, *pityriasis rubra* pilaris, psoriasis, pyoderma gangrenosum, multicentric reticulohistiocytosis, and toxic epidermal necrolysis. Other skin related conditions treatable by the therapies and combination therapies of the present invention include dermatitis herpetiformis.

Additional disorders that can be treated with the antibodies or pharmaceutical compositions of the invention include graft-versus-host disease, and complications resulting from solid organ transplantation, such as heart, liver, skin, kidney, lung (lung transplant airway obliteration) or other transplants, including bone marrow transplants.

Ocular disorders also are treatable or preventable with the disclosed antibodies or pharmaceutical compositions, including rhegmatogenous retinal detachment, and inflammatory eye disease, including inflammatory eye disease associated with smoking and macular degeneration.

Antibodies or pharmaceutical compositions of the invention, as described herein, are useful for treating disorders that affect the female reproductive system. Examples include, but are not limited to, multiple implant failure/infertility; fetal loss syndrome or IV embryo loss (spontaneous abortion); preeclamptic pregnancies or eclampsia; endometriosis, chronic cervicitis, and pre-term labor.

In addition, the antibodies or pharmaceutical compositions of the invention are useful for treating and/or preventing sciatica, symptoms of aging, severe drug reactions (for example, 11-2 toxicity or bleomycin-induced pneumopathy and fibrosis), or to suppress the inflammatory response prior, during or after the transfusion of allogeneic red blood cells in cardiac or other surgery, or in treating a traumatic injury to a limb or joint, such as traumatic knee injury. Various other medical disorders treatable with the disclosed antibodies or pharmaceutical compositions include; multiple sclerosis; Behcet's syndrome; Sjogren's syndrome; autoimmune hemolytic anemia; beta thalassemia; amyotrophic lateral sclerosis (Lou Gehrig's Disease); Parkinson's disease; and tenosynovitis of unknown cause, as well as various autoimmune disorders or diseases associated with hereditary deficiencies, including x-linked mental retardation.

Furthermore, antibodies or pharmaceutical compositions of the invention are useful for treating central nervous system (CNS) injuries, including the effects of neurotoxic neurotransmitters discharged during excitation of inflammation in the central nervous system and to inhibit or prevent the development of glial scars at sites of central nervous system injury. In connection with epilepsy and the treatment of seizures, reducing the severity and number of recurring seizures, and reducing the severity of the deleterious effects of seizures, reducing neuronal loss, neuronal degeneration, and gliosis associated with seizures.

Additional uses for the antibodies or pharmaceutical compositions of the invention include, but are limited to, treating critical illness polyneuropathy and myopathy (CIPNM) acute polyneuropathy; anorexia nervosa; Bell's palsy; chronic fatigue syndrome; transmissible dementia, including Creutzfeld-Jacob disease; demyelinating neuropathy; Guillain-Barre syndrome; vertebral disc disease; Gulf war syndrome; chronic inflammatory demyelinating polyneuropathy, myasthenia gravis; silent cerebral ischemia; sleep disorders, including narcolepsy and sleep apnea; chronic neuronal degeneration; and stroke, including cerebral ischemic diseases. Still additional uses for the antibodies of the invention are anorexia and/or anorexic conditions, peritonitis, endotoxemia and septic shock, granuloma formation, heat stroke. Churg-Strauss syndrome, chronic inflammation following acute infections such as tuberculosis and leprosy, systemic sclerosis and hypertrophic scarring.

Antibodies, modified antibodies or pharmaceutical compositions of the invention are useful for diagnosis diseases described above.

Various indicators that reflect the extent of the patient's illness may be assessed for determining whether the amount and time of the treatment with disclosed antibodies is sufficient.

Any efficacious route of administration may be used to therapeutically administer the antibody. The antibody may be injected via intra-articular, intravenous, intramuscular, intralesional, intraperitoneal, intracranial, inhalation or subcutaneous routes by bolus injection or by continuous infusion. For example, pulmonary diseases can involve intranasal and inhalation methods. Other suitable means of administration include sustained release from implants, aerosol inhalation, eyedrops, oral preparations, including pills, syrups, lozenges or chewing gum, and topical preparations such as lotions, gels, sprays, ointments or other suitable techniques. Administration by inhalation is particularly beneficial when treating diseases associated with pulmonary disorders.

In preferred embodiments, the invention also provides pharmaceutical compositions comprising a therapeutically effective amount of one or a plurality of the antibodies of the invention together with a pharmaceutically acceptable diluent, carrier, solubilizer, emulsifier, preservative and/or adjuvant. Preferably, acceptable formulation materials are nontoxic to recipients at the dosages and concentrations employed. In preferred embodiments, pharmaceutical compositions comprising a therapeutically effective amount of antibodies are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, trimethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, Remington's Pharmaceutical Sciences, 18th Edition, (A. R. Gennaro. ed.), 1990, Mack Publishing Company.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, antibody compositions may be prepared for storage by mixing the selected composition having the desired degree of purity with optional formulation agents (Remington's Pharmaceutical Sciences, supra) in the form of a lyophilized cake or an aqueous solution. Further, in certain embodiments, the antibody product may be formulated as a lyophilizate using appropriate excipients such as sucrose.

The pharmaceutical compositions of the invention can be selected for parenteral delivery. The compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired antibody in a pharmaceutically acceptable vehicle. A particularly suitable vehicle for parenteral injection is sterile distilled water in which the antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, antibodies are formulated as a dry powder for inhalation. In preferred embodiments, antibody inhalation solutions may also be formulated with a propellant for aerosol delivery. In certain embodiments, solutions may be nebulized. Pulmonary administration and formulation methods therefore are further described in International Patent Publication No. WO94/20069, incorporated by reference, which describes pulmonary delivery of chemically modified proteins.

It is also contemplated that formulations can be administered orally. Antibodies that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the antibody. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of antibodies in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, International Patent Publication No. WO93/15722, incorporated by reference, which describes controlled release of porous polymeric microparticles for delivery of pharmaceutical compositions.

Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 22:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., supra) or poly-D(−)-3-hydroxybutyric acid (European Patent Application Publication No. EP 133, 988). Sustained release compositions may also include liposomes that can be prepared by any of several methods known in the art. See e.g., Eppstein et al., 1985, Proc. Natl. Acad. Sci. USA 82:3688-3692; European Patent Application Publication Nos. EP 036,676; EP 088,046 and EP 143,949.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The effective amount of an antibody-containing pharmaceutical composition to be employed therapeutically will depend, for example, upon the therapeutic context and objectives. One skilled in the art will appreciate that the appropriate dosage levels for treatment will vary depending, in part, upon the molecule delivered, the indication for which the antibody is being used, the route of administration, and the size (body weight, body surface or organ size) and/or condition (the age and general health) of the patient. In certain embodiments, the clinician may titer the dosage and modify the route of administration to obtain the optimal therapeutic effect.

A typical dosage may range from about 0.1 μg/kg to up to about 100 mg/kg or more, depending on the factors mentioned above. In preferred embodiments, the dosage may range from 0.1 μg/kg up to about 100 mg/kg; more preferably from 1 μg/kg up to about 100 mg/kg; or even more preferably from 5 μg/kg up to about 100 mg/kg.

Dosing frequency will depend upon the pharmacokinetic parameters of the particular antibody in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter.

Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use antibody pharmaceutical compositions according to the invention ex vivo. In such instances, cells, tissues or organs that have been removed from the patient are exposed to antibody pharmaceutical compositions after which the cells, tissues and/or organs are subsequently implanted back into the patient.

In particular, antibodies can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

In certain embodiments, the invention further encompasses the administration of an antibody or pharmaceutical composition of the invention concurrently with one or more other drugs that are administered to the same patient, each drug being administered according to a regimen suitable for that medicament. This encompasses pre-treatment, simultaneous treatment, sequential treatment and alternating regimens. Examples of such drugs include, but are not limited to, antivirals, antibiotics, analgesics, corticosteroids, antagonists of inflammatory cytokines, disease-modifying anti-rheumatic drugs (DMARDs), non-steroidal anti-inflammatories, anticancer drugs.

In other embodiments, antibody or pharmaceutical composition of the invention can be administered in combination with other cytokine inhibitors, including those that antagonize, for example, RANKL, TGFβ, IFNγ, IL-6 or IL-8 and TNF, particularly TNFα. In combination with IL-6, an antibody of this invention can be used to treat and prevent the recurrence of seizures, including seizures induced by GABAA receptor antagonism, seizures associated with EEG ictal episodes and motor limbic seizures occurring during status epilepticus. In combination with IFNγ inhibitor, an antibody of this invention is useful in treating idiopathic pulmonary fibrosis and cystic fibrosis. The combination of antibody and RANKL inhibitors, e.g. a RANKL antibody is useful for preventing bone destruction in various settings including but not limited to various rheumatic disorders, osteoporosis, multiple myeloma or other malignancies that cause bone degeneration, or anti-tumor therapy aimed at preventing metastasis to bone, or bone destruction associated with prosthesis wear debris or with periodontitis. In addition, antibodies of the invention may be administered in combination with IL-17 inhibitors such soluble forms of an IL-17 receptor (such as IL-17R:Fc) or an IL-17 antibody or IL-17R antibody, IL-18 binding protein, soluble forms of IL-18 receptors, and IL-18 antibodies, antibodies against IL-18 receptors or antibodies against CD30-ligand or against CD4.

The invention further encompasses methods for using an several antibody or pharmaceutical composition of the invention in treating the herein disclosed medical disorders in combination with a TNF inhibitor, and any combination of the above described cytokines or cytokine inhibitors that are active agents in combination therapies. For example, in accordance with the present invention, combination therapy methods may be used for treating rheumatoid arthritis, stroke, asthma, psoriasis, etc.

EXAMPLES

The following examples, including the experiments conducted and results achieved are provided for illustrative purposes only and are not to be construed as limiting the invention.

Example 1

Detection of Potentially Therapeutic Fully Human Antibodies Against VEGF in the Tumor In the present example, detection of potentially therapeutic fully human anti-VEGF antibodies that have infiltrated a tumor comprising the following steps: 1) to obtain biologic materials from patient; 2) to prepare biologic materials for detecting; 3) to identify potentially therapeutic fully human anti-VEGF antibodies in biologic materials; 4) to select fully human anti-VEGF antibodies for further investigation; 5) to characterize of selected fully human anti-VEGF antibodies; 6) to evaluate potent therapeutic activity of the fully human anti-VEGF antibodies.

(1) Exicision of tumor tissue: Fresh tumor specimens from patients were excised aseptically, and tissue was processed under "good laboratory practice" conditions. All resected specimens were sampled for pathologic confirmation of the diagnosis of metastatic renal cell carcinoma.

(2) Preparation of tumor tissue: Each tumor specimen was dissected free of surrounding normal tissue and necrotic areas. Small chunks of tumor (usually 8-20) measuring about 0.5 to 2 mm in each dimension were cut with a sharp scalpel from different areas around the tumor specimen. A single tumor fragment was placed in each tissue culture plate, and then was split and washed twice with RPM-1640 medium to prepare suspension. This suspension was centrifuged at 1,600 r.p.m. for 6 minutes. The tumor supernatant was suspended in 50 ml RPMI-1640 medium and then pipetted into 96-wells plates.

(3) Identification of anti-VEGF antibody

The tumor supernatant in the wells was examined for antibody activity by dot immunobinding assay (DIBA) with human VEGF as antigen, as follows. Recombinant human VEGF (PeproTech) as antigen was dissolved at a concentration of 50 µg/ml in water, then spotted in an amount of 0.2

µl per spot on a nitrocellulose membrane (a product of Toyo) equipped with a grid, and dried in air to immobilize the antigen on the membrane. The immobilized antigen was blocked with a blocking solution (Tris-HCl buffered saline (TBS) containing 10% FCS). 50 µl of the tumor supernatant was put to each well on 96-wells U-bottomed plate, and the blocked, immobilized antigen was then added to it, and the plate was incubated at room temperature for 2 hours. Each well was washed with TBS, and 50 µl peroxidase-labeled anti-human immunoglobulin antibodies (produced by DAKO), previously diluted 500-fold with the blocking solution, was added to each well. The plate was incubated at room temperature for 2 hours. Each well was washed with TBS and stained with Konica Immustein (a product of Konica Corporation) and its coloration was checked with eyes. The same procedure was repeated 30 times for screening of 10,560 samples. As a result, anti-VEGF antibody activity was found in 16 wells.

(4-5) Characterization and Selection of anti-VEGF antibodies for further investigation The aim of isotyping analysis was to identify the specific isotype of the antibodies selected from tumor and to verify their monoclonality. ELISA was used to measure VEGF-specific IgG antibodies in the non diluted tumor supernatant. 96-well maxisorp immunoplates were coated at 4° C. overnight with either recombinant or crude antigens in 0.06 M carbonate buffer (0.04 M NaHCO₃, 0.02 M NaCO₃, pH9.6) in a final volume of 50 µl per well. Non-specific binding was blocked with 5% FCS in carbonate buffer (200 µl/well) for 2 hours at 37° C. Wells were washed three times in Tris buffered saline with 0.1% Tween (TBST) after each step. Isotype specific detection antibodies were diluted in TBST in a final volume of 50 µl per well. Antibody responses to VEGF were determined for IgG isotypes IgG1, IgG2a, IgG2b, IgG3.

Results: Immunoreactivity detected on two tumor supernatants with the anti-IgG1; for one of them, a signal is also detected with an anti-IgG2b. We concluded that IgG1 antibody is a most likely monoclonal. These results also suggest that other antibody is not monoclonal due to the detection of 2 different isotypes (IgG1 and IgG2b) on the tumor supernatant. Thus, only one anti-VEGF antibody was selected for further investigation.

High-performance liquid chromatography with tandem mass spectrometry detection (HPLC-MS/MS) is a widely-used method for quantitating small molecule pharmaceuticals from biological matrices. A triple quadrupole mass spectrometer operating in multiple-reaction monitoring mode (MRM) typically provides the lowest LOQs, highest specificity, best precision and accuracy and highest throughput, although other types of mass spectrometry methods may also be employed. Only recently has this technology been extended to the quantitation of proteins from complex samples such as serum and cell lysates (Gerber et. al. (2003). This technology is also described for detection of antibody-drug conjugates in PCT patent application [Miryam Kadkhodayan, et al. WO2005101017]. Similar method is also described for identification and sequencing of proteins [Pavel Pevzner, et al. US20110015863] and other authors [Brian Walter Granda, et al. US20100015652], etc.

Using liquid chromatography with tandem mass spectrometry and complete protein sequencing as described by Stoll et al. (2015), structure of anti-VEGF antibody with light

```
SEQ ID NO 1:
Structure of anti-VEGF antibody, light chains
as example
ARAPSIVTTLSKVFPPEQLLKSGATSDSVCVNFPYRTHQEAKVQWKVAGQ

NSETESVQSDKDSTFTLYSVYSKSADNDYEKHACELLNVGLSSPVGETFK

SNRLQSC

SEQ ID NO 2:
Structure of anti-VEGF antibody, heavy chains
as example
PGKSKSYFTPSVYPLIGSALNGAQTNSCRVNSATFPESKLNVPVTVTWNS

GVHTFPAVLESDLYTLSSSVPTESSPRPSETVTVVDCNSTKVDKDDVEVH

TAKIPRQPDCGCKPCICTPEIFPAKPKDVLTTITLTPKCVISKDDGYPEV

QFSVAHPASWFVQTREEQFNSVSSVFTFRSVSETNLPIMHQDWKEFKFPA

PIEKTITAKKRPKAPQVYTIPLGCLVKPPKEQMAKDKVSLTYQKCMPITD

FFPEDAPTVEWQWNGMVQPAENYKNTQPIMNGVSNWEGSLSSAGNTFTCS

VTVLHEGLHNPHHKSLSHST
``` chains was determined. Based on the results, PCR amplification and DNA maxi-preparation were performed. CHO-S cells were seeded at 10₆ cells/mL the day of transfection of DNA. Ratio DNA/max reagent (Invitrogen) was ratio 1/1. Conditions of culture were CHO-SFMII medium (serum free medium), 37° C., 8% CO₂ under shaking. Cells and culture supernatant were harvested 3, 4 and 5 days post transfection by centrifugation 200 g, 5 min. After purification Western Blot analysis for production monitoring and ELISA analysis with coating of the antigen were performed. These analyses confirmed expression of selected antibody by CHO-S cells. Results of BIAcore analysis showed that recombinant anti-VEGF antibody has high affinity (Kd (M) $1.1 \times 10_{-9}$; Koff(1/s) $1.3 \times 10_{-4}$) to the VEGF A (UniProt number 15692).

(6) Evaluation of the potent therapeutic activity of selected anti-VEGF fully human antibody The effect of the human monoclonal antibody on the wandering activity of vascular endothelial cells induced by human VEGF as one step of vascularization was examine. Human umbilical venous endothelial cells (HUVEC) cells were plated into 24-well plates and were cultured in DMEM containing 10% FCS, 2 mmol/L L-glutamine, and 1% penicillin/streptomycin for 24 hours. Anti-VEGF fully human antibody (10 mcg/mL) or vehicle (0.01% DMSO in DMEM) were added to the cultures. Bevacizumab (Genentech; 10 mcg/mL) was used as a positive control. VEGF A (BD Bioscience) was added at a concentration of 100 ng/ml. Endothelial cell proliferation was determined. Anti-VEGF fully human antibody significantly inhibited proliferation of HUVEC cells in comparison with vehicle ($P<0.0001$) or bevacizumab ($P<0.001$). FIG. 1.

Figure 2:
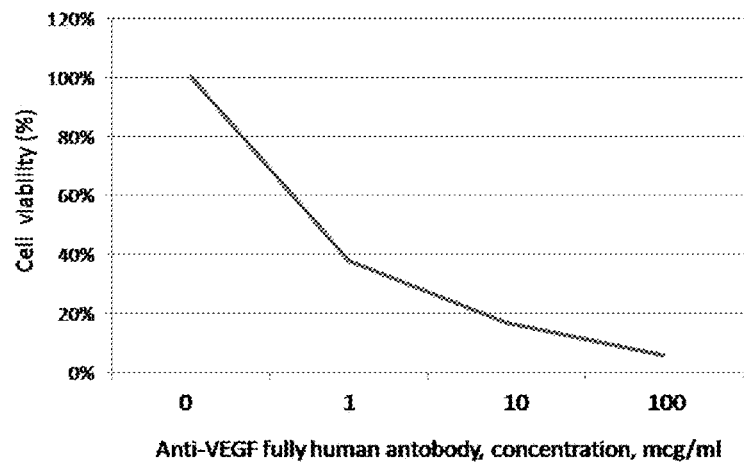
FIG. 2. Inhibitory effects of anti-VEGF fully human antibody of the present invention on cancer cells proliferation in vitro FIG. 3. Anti-VEGF fully human antibody of the present invention inhibited tumor growth compared with anti-VEGF humanized antibody and vehicle in vivo.

To assess the effect of anti-VEGF fully human antibody on VEGF-mediated signaling, the human renal carcinoma Caki-1 cells were dosed with anti-VEGF fully human antibody at 100, 10, and 1 mcg/ml. Control wells were left untreated. Three hours after dosing, VEGF A was added at a concentration of 100 ng/ml. Additional control wells were treated with anti-VEGF fully human antibody without VEGF-stimulation. Cell growth inhibition was determined using Promega's Cell Titer-Glow® assay. In vitro study showed that VEGF A increased proliferation of the human renal carcinoma cells ($P<0.0001$). Anti-VEGF fully human antibody dose dependently inhibited VEGF-triggered cell proliferation in comparison with control ($P<0.0001$), FIG. 2.

Figure 3:
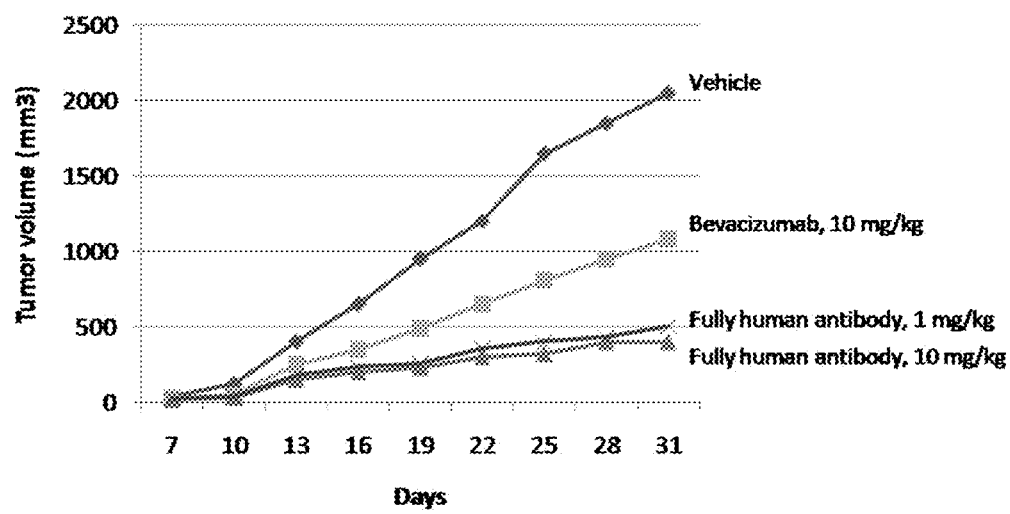

CR female NCr nu/nu mice were set up with 1 mm₃ Caki-1 tumor fragments subcutaneously into the right flank. Tumor sizes were measured in a blind fashion twice a week with a vernier caliper. Mice with established tumors were randomly divided into vehicle, bevacizumab or anti-VEGF fully human antibody groups per 10 animals in group. Endpoint was significant differences in tumor growth delay. In vivo, the tumors in untreated mice or mice treated with bevacizumab (10 mg/kg) continued their aggressive growth to reach the size of 2000 cm3, at which point the mice were killed. In contrast, treatment with anti-VEGF fully human antibody not only significant arrested further growth of the tumors ($P<0.0001$) but also demonstrated differences in tumor volume compared with vehicle already on Day 10; FIG. 3. A similar anti-tumor activity of anti-VEGF fully human antibody was observed when the antibody was given in low (1 mg/kg) or high (10 mg/kg) doses ($P=0.7$). Administration of 10 mg/kg antibody for up to 35 days resulted in minimal body weight loss and no observations of gross toxicity were made.

Anti-VEGF fully human antibody of the present invention has been derived from tumor tissue and demonstrated therapeutic potential.

Example 2

Detection of Potentially Therapeutic Fully Human Antibodies in the Placenta

In the present example we demonstrate that potentially therapeutic fully human antibodies could be detected in human placenta. The detection of potentially therapeutic fully human antibodies that have infiltrated a placenta comprising the following steps: 1) to obtain placenta from healthy women or patients; 2) to prepare biologic materials for detecting; 3) to identify potentially therapeutic fully human antibodies in biologic materials; 4) to select fully human antibodies for further investigation; 5) to characterize of selected fully human antibodies; 6) to evaluate potent therapeutic activity of the fully human antibodies.

(1) Tissue sample collection: All patients signed informed consent. Placentas were obtained from patients with uncomplicated pregnancies delivering at term or from pregnancies with small for gestational age infants or preterm labor including preeclampsia cases with decidual vasculopathy. Placental and decidual tissues were collected as previously described by Staff et al. (Am J Obstet Gynecol 1999; 180:587-92) and Harsem et al. (Acta Obstet Gynecol Scand. 2004 August; 83(8):724-30). The collected samples were divided into two parts: the first portion was fixed in 10% formaldehyde solution and paraffin-embedded for immunohistochemical staining, whereas the remaining portion was placed in cold PhysioSol solution (Abbott Laboratories, IL. USA) and was used within 12 hours of the tissue acquisition for further study. The molecular characteristics of these groups were analyzed. The expression levels of VEGF, vascular endothelial growth factor receptors (VEGFRs), fibroblast growth factor (FGF), fibroblast growth factor receptors (FGFRs), epidermal growth factor (EGF), epidermal growth factor receptors (EGFRs), and platelet-derived growth factor receptors (PDGFRs) in the placenta and decidua were detected through immunohistochemistry, reverse-transcription polymerase chain reaction, and Western blot. Placentas with high expression levels of FGFR and EGFR were used with aim to detect anti-FGFR1 and anti-EGFR potentially therapeutic fully human antibodies as example. The other aim was to detect anti-TNF-α potentially therapeutic fully human antibodies as another example.

(2) Placenta preparation: Each tissue specimen was dissected free of surrounding vascular fibrinoid necrosis and lipid areas. Small chunks (usually 10-20) of placenta (preferably vascular area) measuring about 0.5 to 1.5 mm in each dimension were cut with a sharp scalpel from different areas around the specimen. Some of the tissue samples were run on Tris-Tricine 4-20% SDS polyacrylamide gradient gels followed by silver staining to separate protein bands (5~200 kDa). Samples were diluted 1:10 with sample buffer containing 0.5% β-mercaptoethanol and incubated at 95° C. at a Perkin Elmer thermocycler (Santa Clara, Calif., USA) for 10 min. After gel-electrophoresis, the gel was exposed to Bio-Rad silver staining solution (Hercules, Calif., USA) for 15-20 min.

(3) Identification of anti-EGFR antibody, anti-FGFR antibody and anti-TNF-α antibody by liquid chromatography in-line with tandem mass spectrometry (LC-MS/MS)

Each sample was transferred to a new sterile Eppendorf tube and proteins were denatured in 100 μl of 50 mM Tris pH 8.5 buffer containing 8 M urea and 100 mM β-mercaptoethanol. Samples were lysed by passage through a 25 gauge needle using a 1 mL syringe and 50 μg total protein was prepared for MS analysis. Samples were reduced with 10 mM dithiothreitol for 1 hour at 37° C. and then alkylated with 55 mM iodoacetamide for 1 hour at room temperature in the dark. After alkylation, samples were diluted with 50 mM Tris buffer pH 8.5 to have 0.5 M final urea concentration (1/16 dilution) and digested with trypsin overnight. Peptides were acidified with o-phosphoric acid and 1% acetonitrile was added. Samples were desalted using a C18 microspin cartridge (The Nest Group, MA, USA). Desalted samples were then applied to a SCX microspin cartridge (The Nest Group, MA, USA) and eluted using 4 different salt concentrations (20, 40, 60, and 120 mM KCl) according to manufacturer's protocol. Eluted peptides were desalted and applied to an LC column in-line with the mass spectrometer. After separation of peptides, MS data were recorded on a LTQ-XL linear ion trap mass spectrometer (Thermo Fisher Scientific, MA, USA). A 90 minute gradient was applied for all the peptide separations on the LC column. Proteins were identified via two automated databases (a subset of the SwissProt 2012_09 and the SwissProt 2012_09 databases, 20,235 entries) and two search engines (Mascot Search Engine (version 2.4.0, Matrix Science, MA, USA) and X! Tandem (version cyclone, GPM)). The identified proteins by LC-MS/MS analysis with a minimum 2 peptides and 0% false discovery rate (FDR) were afforded by Mascot Search Engine. Maximum missed cleavages for trypsin were set to 2. Cysteine carbamodimethylation was used as fixed and methionine oxidation was used as variable modification. Mass tolerance for the parent ions was set to 1.8 Da and mass tolerance for fragment ions was set to 0.4 Da. To determine reproducibility, the same protein sample was analyzed 3× using the identical LC-MS/MS method. The initial run identified 58 proteins (100%), the second run, 59 proteins (91%) and the third run, 57 proteins (98%). Next step included confirmation of specific anti-FGFR antibody, anti-EGFR antibody and anti-TNF-α antibody. We used radiolabeled proteins (EGFR, FGFR1 and TNF-α), but other identified methods could be used. Radiolabeled proteins EGFR, FGFR1 and TNF-α were immunoprecipitated with a potential antibodies and evaluated. After selection of proteins, one more run of LC-MS/MS identified antibodies in placenta samples. Immunobinding assay described in Example 1 (3) with human EGFR, FGFR1 and TNF-α as antigens confirmed activity of anti-EGFR antibody, anti-EGFR antibody and anti-TNF-α antibody, respectively.

(4-5) Characterization and Selection of anti-EGFR antibody, anti-FGFR antibody and anti-TNF-α antibody for further investigation Based on results of identification, we performed isotyping analysis to identify the specific isotype of the antibodies selected from placenta and to verify their monoclonality. Methods for characterization and selection described above (Example 1 (4-5) were used. Selected anti-EGFR antibody was fully human monoclonal IgG2 with high affinity (Kd (M) $8.3\times10.9$) to the human EGFR (UniProt number P00533). Selected anti-FGFR1 antibody was fully human monoclonal IgG1 with high affinity (Kd (M) $10\times10_{-10}$) to the human FGFR1 (UniProt number P11362). Selected anti-TNF-α antibody was fully human monoclonal IgG1 with high affinity (Kd (M) $6.7\times10_{-9}$) to the human TNF-α (UniProt number P01375).

(6) Evaluation of the potent therapeutic activity of fully human antibodies detected in the human placenta In the present investigation, breast cancer cell line, MDA-MB-468, was utilized. The reason for choosing this cell line is that it express high levels of EGFR as depicted later. The cell line was maintained in DMEM medium supplemented with 10% fetal bovine serum, 100 units/mL streptomycin-penicillin, and incubated at 37° C. in an atmosphere of 95% air and 5% $CO_2$. The viability of cells was assessed using 3-(4,5-dimethylthiazol-2-yl)-2,5-diphenyltetrazolium bromide (Sigma-Aldrich) assays. Briefly, cells were seeded in complete growth medium in 96-well plates at a density of 3,000 per well. Following overnight incubation, cells were grown for 24 h in medium supplemented with or without 0.1%, 1%, and 10% serum and/or EGF and then incubated for an additional 72 h in the presence of the anti-EGFR fully human antibody or cetuximab (Merck Serono). Concentrations of treatment drugs were 0.1, 1, 10 mcg/mL.

Figure 4:
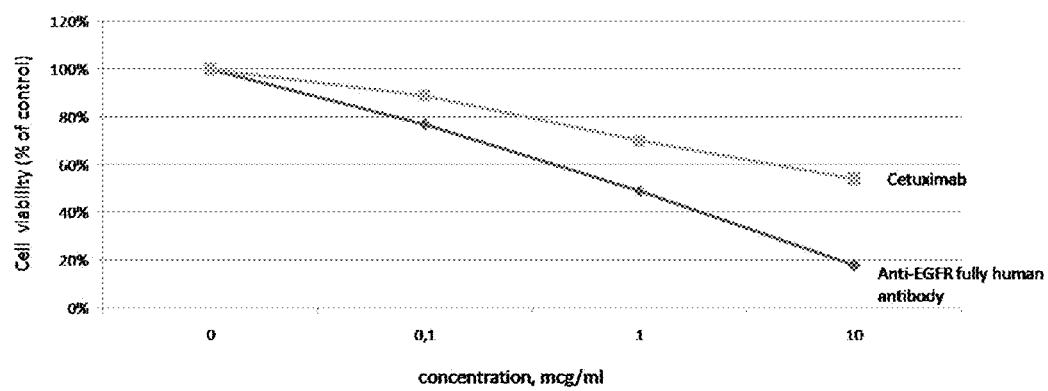
FIG. 4. Anti-EGFR fully human antibody of the present invention inhibits MDA-MB-468 breast cancer cells proliferation.

Anti-EGFR fully human antibody significantly inhibited EGF-stimulated proliferation of breast cancer cells in comparison with cetuximab (P<0.0001), FIG. 4. The effect of inhibition was dose-dependent.

Six- to 8-week-old female BALB/c athymic mice were purchased. The initial body weight of the animals at the time of arrival was between 18 and 20 g. Mice were allowed to acclimatize to local conditions for 1 week before being injected with cancer cells. Tumors were induced by injecting HCT116 colon cancer cells ($5\times10_6$) subcutaneously into the right flank of mice. The tumors were then measured twice a week using calipers, and the tumor volume ($mm_3$) was calculated according to following formula: [(width$_2\times$height)/2]. When tumors had reached a volume of 50 $mm_3$, treatment with anti-EGFR fully human antibody of the present invention or cetuximab, or a vehicle control (saline) was initiated. A dose of 10 mg/kg of anti-EGFR fully human antibody and dose of 10 mg/kg of cetuximab was given i.p. twice a week.

Figure 5:
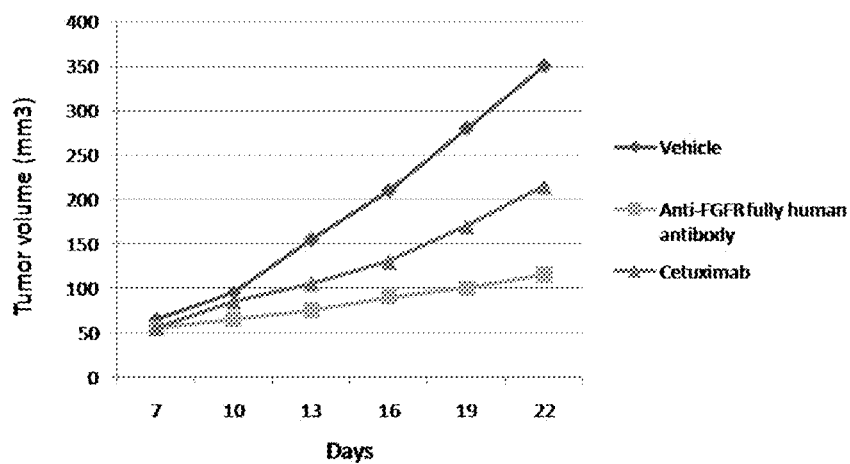
FIG. 5. Anti-EGFR fully human antibody of the present invention significantly inhibits growth of colon cancer xenograft.

Treatment with anti-EGFR fully human antibody and cetuximab resulted in significant tumor growth delay compared with vehicle (P<0.001). Anti-EGFR fully human antibody was more effective than cetuximab. The median tumor volume was 105, 215 and 390 mm3 on Day 22 for anti-EGFR fully human antibody, cetuximab and vehicle, respectively; FIG. 5.

Our findings showed that anti-EGFR fully human antibody of the present invention has potent antitumor activity against cancer in vitro and in vivo.

Figure 6:
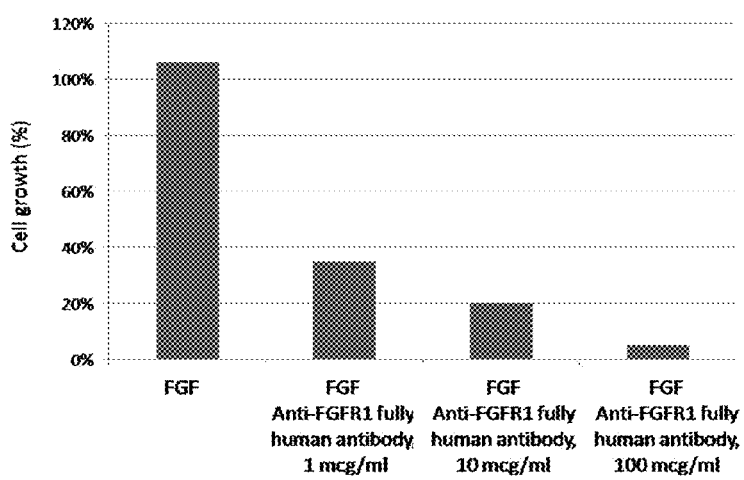
FIG. 6. Anti-FGFR1 fully human antibody of the present invention dose dependently inhibited proliferation of lung cancer cells.

To assess the effect of anti-FGFR1 fully human antibody of the present invention on FGF-mediated signaling, the human lung cancer A549 FGFR1-expressing cells were incubated (0.5% FBS) and were dosed with anti-FGFR1 fully human antibody. Control cells were left untreated. Four hours after dosing, basic FGF was added at a concentration of 50 ng/ml. Cells growth was determined using Promega's Cell Titer-Glo® assay. In vitro study showed that basic FGF significantly increased proliferation of the human lung cancer cells (P<0.001). Anti-FGFR1 fully human antibody exerted dose-dependent inhibitory effects on FGF-triggered lung cancer cell proliferation in comparison with control (P=0.001); FIG. 6. Growth inhibitory concentration 50 (GI50) was 18.5 ng/mL.

Figure 7:
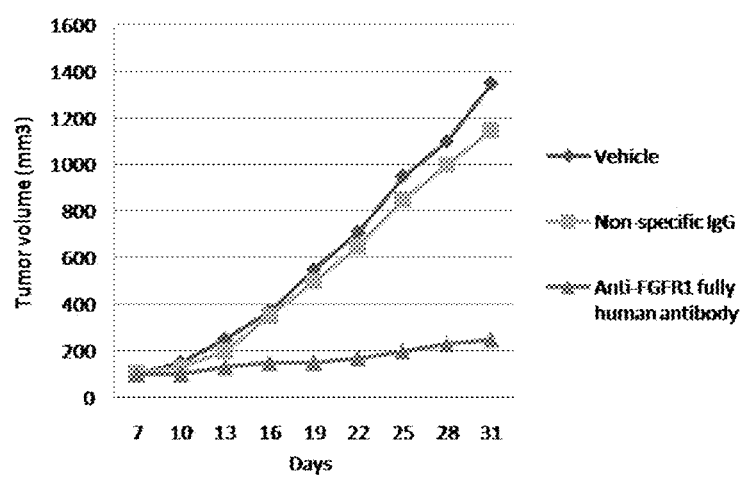
FIG. 7. Anti-FGFR1 fully human antibody of the present invention significantly inhibits growth of lung cancer xenograft.

In vivo, thirty-five NCr nu/nu female mice (10-12 weeks of age) were used for A549 xenotransplantation. Thirty animals with measurable tumors were pair matched and selected on day 7 after tumor inoculation. Intravenous anti-FGFR1 fully human antibody (10 mg/kg, N=10) or non-specific IgG (10 mg/kg, N=10) or saline (Vehicle, N=10) were administered every 3 days starting on day 7 after tumor inoculation. Measurements of tumor volume ($mm_3$) were performed by digital calipers every 3 days during 31 days. No group mean body weight losses or clinical manifestations of toxicity were observed. In anti-FGFR1 fully human antibody, non-specific IgG and vehicle groups, treatment resulted in median tumor volume of 250 $mm_3$, 1150 $mm_3$ and 1350 $mm_3$ on day 31, respectively. Differences between fully human antibody and other groups were statistically significant (P<0.0001); FIG. 7.

Our findings showed that anti-FGFR1 fully human antibody of the present invention has potent antitumor activity against cancer in vitro and in vivo.

To compare efficacy of fully human antibody of the present invention with efficacy of fully human antibody that received using other technology, anti-EGFR fully human antibody of the present invention described above and panitumumab (Amgen, anti-EGFR fully human antibody) were used. Six-week-old female BALB/c athymic mice were purchased. The initial body weight of the animals at the time of arrival was 20 g. Mice were allowed to acclimatize to local conditions for 1 week before being injected with cancer cells. Tumors were induced by injecting HCT116 colon cancer cells ($5\times10_6$) subcutaneously into the right flank of mice. The tumors were then measured twice a week using calipers, and the tumor volume ($mm_3$) was calculated according to following formula: [(width$_2\times$height)/2]. When tumors had reached a volume of 100 $mm_3$, treatment with anti-EGFR fully human antibody of the present invention (N=10) or panitumumab (N=10), was initiated. A dose of 3 mg/kg of anti-EGFR fully human antibody and dose of 3 mg/kg of panitumumab was given i.p. twice a week.

Figure 8:
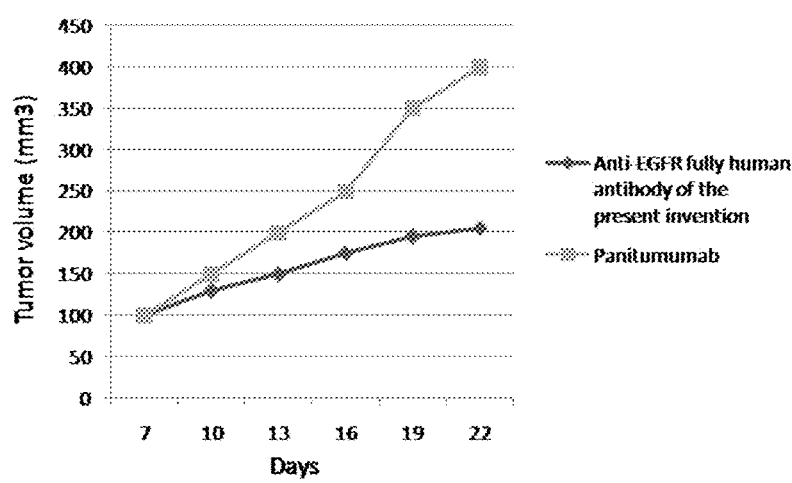
FIG. 8. Anti-EGFR fully human antibody of the present invention is more effective than other fully human antibody (panitumumab) in vivo.

Treatment with anti-EGFR fully human antibody resulted in significant tumor growth delay compared with panitumumab (P=0.01). The median tumor volume was 205 and 600 mm3 on Day 22 for anti-EGFR fully human antibody and panitumumab, respectively; FIG. 8.

This study confirmed that fully human antibody of the present invention could be more effective than fully human antibodies that received using other technologies.

To investigate anti-inflammatory effects of anti-TNF alpha fully human antibody of the present invention, D-galactosamine sensitized murine in vivo model was used. Groups of 10 female C57BL/6 mice were treated i.p. with 1, 10 and 50 ng of anti-TNF alpha fully human antibody followed 30 minutes later by a 20 mg i.p. injection of rhTNF alpha mixed with D-galactosamine. Saline and non-specific IgG (50 ng) were used as vehicle. The mice were observed 24 hours after treatment, and the present survival was determined. The percent survival at 24 hours after treatment is shown in the table below (Table 1). Treatment with anti-TNF alpha fully human antibody resulted in a dose dependent increase in survival.

TABLE 1

Anti-TNF alpha fully human antibody of the present invention increased survival in vivo

| Study group | Number of survived mice | Survival, % |
| --- | --- | --- |
| Saline | 0/10 | 0 |
| Non-specific IgG | 0/10 | 0 |
| Anti-TNF alpha fully human antibody, 1 ng | 2/10 | 20 |
| Anti-TNF alpha fully human antibody, 10 ng | 5/10 | 50 |
| Anti-TNF alpha fully human antibody, 50 ng | 9/10 | 90 |

The invention claimed is:

1. A method for identification of therapeutic and diagnostic high-affinity fully human antibodies that have infiltrated a human tissue; said method comprising the steps of:
   (a) obtaining and preparing said human tissue supernatants and/or lysates from patients and donors;
   (b) contacting step (a) with an antigen of interest;
   (c) identifying fully human antibody from step (b) by binding assay;
   (d) Isotyping the fully human antibody and selecting the high-affinity fully human antibody from step (c);
   (e) Evaluating of said selected high-affinity fully human antibody by treating tissue of interest with said selected high-affinity fully human antibody and evaluating its effect thereof;
   (f) Establishing production and purification of a recombinant of said high-affinity fully human antibody for therapeutic and diagnostic use.

2. The method of claim 1 wherein said human tissue is a tumor.

3. The method of claim 1 wherein said human tissue is placenta, decidual tissues or hydatidiform moles.

4. The method of claim 1 wherein said human tissue is blood plasma, lymph fluid, synovial fluid, cell-free exudates or spinal cord fluid of said individual.

5. The method of claim 1 wherein said therapeutic high-affinity fully human antibodies are antibodies for treatment of human diseases.

6. The method of claim 1 wherein said diagnostic high-affinity fully human antibodies are antibodies for diagnosis of human diseases.

7. The method of claim 1 wherein said high-affinity fully human antibodies are human monoclonal or polyclonal antibodies.

8. The method of claim 1 wherein said high-affinity fully human antibodies are human modified antibodies or their fragments.

* * * * *